United States Patent
Ding et al.

(10) Patent No.: US 9,611,203 B2
(45) Date of Patent: *Apr. 4, 2017

(54) METHOD FOR OLEFIN HYDROFORMYLATION REACTION USING SOLID HETEROGENEOUS CATALYST

(71) Applicant: DALIAN INSTITUTE OF CHEMICAL PHYSICS, CHINESE ACADEMY OF SCIENCES, Dalian (CN)

(72) Inventors: Yunjie Ding, Dalian (CN); Li Yan, Dalian (CN); Miao Jiang, Dalian (CN); Ronghe Lin, Dalian (CN)

(73) Assignee: DALIAN INSTITUTE OF CHEMICAL PHYSICS, CHINESE ACADEMY OF SCIENCES, Dalian (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/102,407

(22) PCT Filed: Dec. 11, 2013

(86) PCT No.: PCT/CN2013/089048
§ 371 (c)(1),
(2) Date: Jun. 7, 2016

(87) PCT Pub. No.: WO2015/085503
PCT Pub. Date: Jun. 18, 2015

(65) Prior Publication Data
US 2016/0318835 A1 Nov. 3, 2016

(51) Int. Cl.
*C07C 45/50* (2006.01)
*B01J 31/00* (2006.01)
*B01J 31/24* (2006.01)

(52) U.S. Cl.
CPC ............... *C07C 45/50* (2013.01); *B01J 31/24* (2013.01); *B01J 31/2404* (2013.01); *B01J 2231/321* (2013.01); *B01J 2531/822* (2013.01)

(58) Field of Classification Search
CPC ........ C07C 45/50; B01J 31/24; B01J 31/2404
USPC .......................................................... 568/454
See application file for complete search history.

(56) References Cited

U.S. PATENT DOCUMENTS

| 4,148,830 A | 4/1979 | Pruett |
| 4,252,678 A | 2/1981 | Smith |
| 6,229,052 B1 | 5/2001 | Bunel |

FOREIGN PATENT DOCUMENTS

| CN | 1043640 | 7/1990 |
| CN | 102281948 | 12/2011 |
| CN | 102617308 | 8/2012 |
| CN | 102649715 | 8/2012 |

OTHER PUBLICATIONS

Li et al., "Study on the Suzuki Coupling Reaction Catalyzed by Palladium Catalyst supported in Microcapsule Film" CMFD, No. 8 (2008) (English abstract is included.).

*Primary Examiner* — Sikarl Witherspoon
(74) *Attorney, Agent, or Firm* — Enshan Hong; VLP Law Group LLP

(57) ABSTRACT

A method for an olefin hydroformylation reaction comprising subjecting olefins and CO/H2 mixed gas to the olefin hydroformylation reaction in a reactor in the presence of a solid heterogeneous catalyst, which consisting of a metal component and an organic ligand polymer with hierarchical porosity, in which the metal component is one or more of Rh, Ir or Co, the organic ligand polymer is a polymer formed by polymerization of an organic ligand monomer containing P and alkenyl group and optional N, and in the solid heterogeneous catalyst, the metal component forms coordinated bonds with the P atom or N in the backbone of the organic ligand polymer and exists in a monoatomic dispersion state; the reaction technique and device are simple, and the catalyst has a stable hydroformylation property with a high activity and yield.

10 Claims, 1 Drawing Sheet

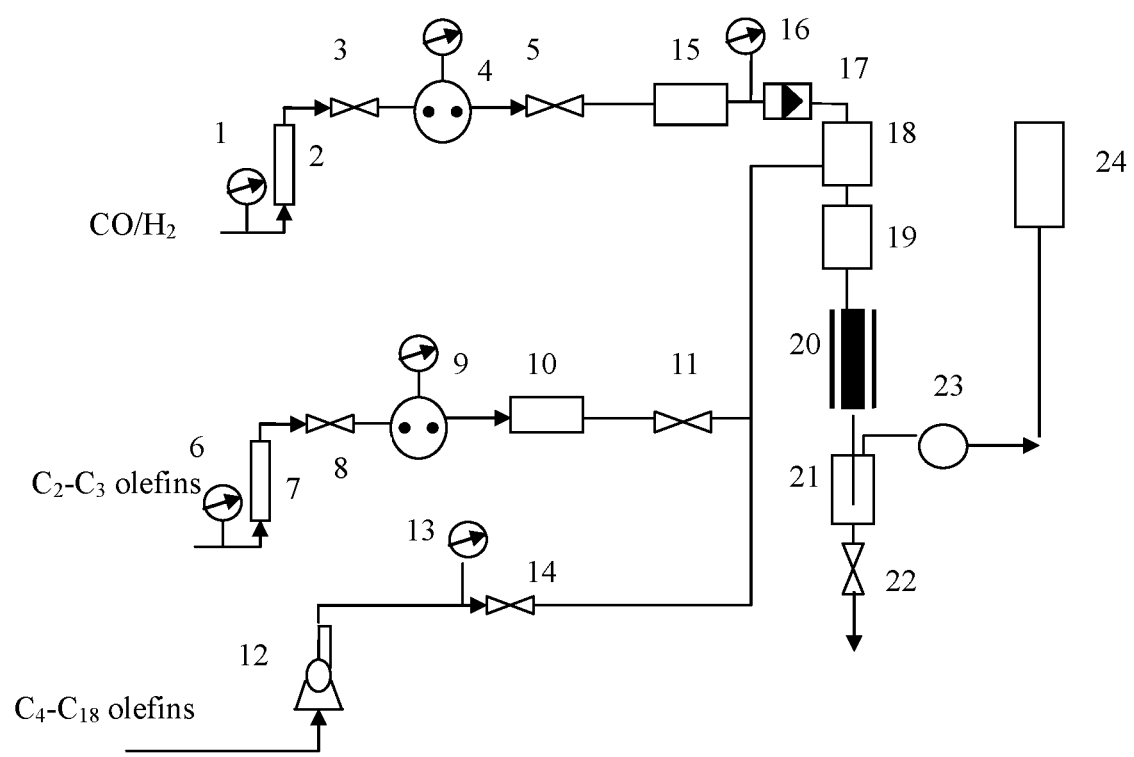

METHOD FOR OLEFIN HYDROFORMYLATION REACTION USING SOLID HETEROGENEOUS CATALYST

RELATED APPLICATIONS

This is a U.S. national stage of international application No. PCT/CN2013/089048 filed on Dec. 11, 2013.

FIELD OF THE INVENTION

The present invention relates to a method for catalyzing olefin hydroformylation reaction by using a novel solid heterogeneous catalyst, and belongs to the field of heterogeneous catalytic techniques.

BACKGROUND

Hydroformylation reaction is the reaction that an aldehyde is produced by a reaction between olefins and syngas ($CO+H_2$), wherein the number of carbon atoms of the aldehyde is one more than that of the olefin. The main reason why the hydroformylation technique is widely used in the chemical industry and becomes one of the most important techniques is that the product thereof, aldehydes, is a very useful chemical intermediate. Aldehydes can be used to synthesize carboxylic acids and corresponding esters, and aliphatic amines, etc. The most important application of aldehydes is that they can be converted to alcohols by hydrogenation. Alcohols per se can be widely used as organic solvents, plasticizers, surfactants, or the like in fine chemical engineering field. The study on hydroformylation reaction, especially on the industrialization thereof, is becoming wider and deeper, as the demands for aldehydes and alcohols increase in the industry of fine chemicals, such as plastics, coatings, rubbers, and detergents, which are closely associated with daily life.

CN 102617308 A discloses an olefin biphasic hydroformylation method. The complex catalyst used in the method is formed by polyether guandinium mesylate ionic liquids (PGMILs) with room temperature solidifiable characteristics, $RhCl_3 \cdot 3H_2O$ or dicarbonylacetylacetonato rhodium, and triphenylphosphine-3,3',3"-trisulfonic acid sodium (TPPTS). The reaction is carried out in an autoclave made of stainless steel. The selectivity of high-carbon aldehydes is up to 85~99%. The molar ratio of normal aldehydes to isomeric aldehydes is from 2.0 to 2.4. However, the reaction uses an ionic liquid, which is expensive and complex to be produced. Rh lost into the product phase is from 0.04% to 0.07%. Although the ionic liquid has advantages such as having a high melting point, having no volatility, and the like, the price thereof is relatively high. In particular, for a high-purity ionic liquid, the purification is complex, and the cost for production is high, which limits the application in industry to certain extent.

CN 102649715 A discloses a method for preparing aldehydes by olefin hydroformylation. In the method, $C_2$-$C_8$ olefins, CO and hydrogen gas are used as raw materials, and an Rh-containing liquid solution is used as the catalyst. The raw materials and the Rh-containing liquid solution catalyst are fed into a highly efficient reactor, being in contact with each other and reacting, to produce a liquid effluent containing aldehydes. The highly efficient reactor used therein is selected from rotating packed bed reactors. U.S. Pat. No. 4,148,830 discloses a hydroformylation method using a liquid phase recycle process. In this method, the resultant aldehyde condensation product is used as a solvent for catalyst. Once the aldehyde product is recovered from the product stream, the medium containing the catalyst is recycled back to the hydroformylation reaction zone. However, in this method, there are some problems in separation of the reaction products and in recovery of the catalyst dissolved uniformly in the reaction products.

U.S. Pat. No. 6,229,052 discloses a hydroformylation reaction, wherein Rh/grafted polymer is used as a fixed bed for catalyzing propylene in gas phase. The gas phase catalytic reaction gives results similar to those of the slurry bed, namely not only the conversion and the activity are relatively low, but also a significant decrease of the activity of the catalyst is observed.

U.S. Pat. No. 4,252,678 discloses the production of a colloidal dispersion containing a transition metal, such as Rh, etc. In this process, the catalyst system is consisted of a transition metal component in form of a colloidal dispersion of 1.0 to 20.0 nm and (styrene/butadiene) functionalized copolymer terminated by a hydroxy group, and is used in the hydroformylation reaction of 1-octene. The catalyst prepared by this method cannot be used in fixed bed reactors and trickle bed reactors, and it is difficult to separate the catalyst from the product.

CN 102281948 A reports polymer-supported transition metal catalyst complexes and methods for use, and produces soluble polymer-supported rhodium catalysts that have a narrow molecular weight distribution. However, all the processes for production of the catalyst, the catalytic reaction, and separation of the catalyst are complex. In the production of the catalyst, it is required to synthesize a soluble polymer by controlling functional monomers and styrene, etc., and then introduce a ligand, and at last support the Rh catalyst. It is required to add compressed gas during the catalytic reaction. The catalyst is separated from the reaction mixture by means of nanofiltration, and the reaction result is not ideal, either.

The paper "*Study on the Suzuki Coupling Reaction Catalyzed by Palladium Catalyst supported in Microcapsule Film*" (Kaixiao L I, CMFD, No. 8) reports that a Pd-based catalyst is produced by using a microcapsule material, in which phosphorus ligands are connected in the polystyrene microcapsule film, as the support, and used in Suzuki coupling reaction. However, the microcapsule material is a copolymer material, rather than a monopolymer material. The dispersion state of the transition metal component in this catalyst is not mentioned.

In the current industrial production of aldehydes from olefin hydroformylation reaction, Rh-based homogenous catalytic technique and cobalt-based homogeneous catalytic technique are mainly used. Although the reaction activity and selectivity of homogeneous catalysts cannot be achieved by those heterogeneous catalysts, many homogeneous catalysts cannot be scaled up, only because it is difficult to separate the catalyst from the product. During the production, the activity of a catalyst decreases slowly, so it is necessary to discharge a part of the catalyst continuously, while complementing an equal amount of catalyst. Since the price of Rh is high, it is necessary to recover Rh from the stream discharged. The process of this treatment is complex, and causes burden in the production.

Recently, the study of the heterogenization of homogeneous catalysts is of wide interest. The heterogenization techniques of homogeneous catalysts are mainly classified into two categories. One is immobilization of homogeneous catalyst, including immobilization by inorganic supports, immobilization by polymer supports, supported liquid phase catalysts, and supported aqueous phase catalysts. The other is a biphasic catalysis, including liquid/liquid biphasic catalysis, fluorine biphasic system, temperature-controlled phase separation catalysis, supercritical fluid biphasic system, ionic liquid biphasic system and supercritical fluid-ionic liquid biphasic system. Many novel concepts come forth from these catalytic systems. However, in these systems, the loss of active metal is great, or the stability of catalysts is poor, or expansive organic ligands or solvents are used, or the production of the catalyst has a heavy and complicated procedure, complex techniques, and the like, so that all of these systems cannot meet the requirements for industrial production. Concerning heterogeneous catalytic systems, there are only a few reports about improving the catalytic property of a heterogeneous catalyst by adding metal auxiliaries thereto. However, since the catalytic activity of these systems is much lower than those of homogeneous catalytic systems, these systems cannot meet the requirements for industrial production, either.

SUMMARY OF INVENTION

Directed to the disadvantages in the prior art, the object of the invention is to provide a heterogeneous hydroformylation reaction process, which uses highly active solid heterogeneous catalyst and is easily realized industrially.

For this purpose, the invention provides a method for olefin hydroformylation reaction, wherein the method uses a solid heterogeneous catalyst consisted of a metal component and an organic ligand polymer with hierarchical porosity, wherein the metal component is one or more of Rh, Ir or Co, the organic ligand polymer is a polymer formed by polymerization of an organic ligand monomer containing P and alkenyl group and optional N, the metal component forms coordinated bonds with the P atom or N in backbone of the organic ligand polymer and exists in a monoatomic dispersion state in the solid heterogeneous catalyst, the method comprises subjecting olefins and a $CO/H_2$ mixed gas to the olefin hydroformylation reaction in a reactor in the presence of the solid heterogeneous catalyst.

In a preferred embodiment, the olefin is one or more of $C_2$ to $C_{18}$ olefins, and the molar ratio of the olefin to the $CO/H_2$ mixed gas is 0.1:1 to 1:1.

In a preferred embodiment, when the olefin is a $C_2$ to $C_3$ gaseous olefin, it is fed in the form of gas directly at a volume space velocity of 100 to 20000 $h^{-1}$; when the olefin is a $C_4$ to $C_{18}$ liquid olefin, it is transported into a reaction system by a high-pressure pump at a mass space velocity of 0.01 to 10 $h^{-1}$.

In a preferred embodiment, the reactor is a fixed bed, a trickle bed, or an autoclave reactor.

In a preferred embodiment, the olefin hydroformylation reaction is carried out in an intermittent manner or in a continuous manner.

In a preferred embodiment, the reaction temperature of the olefin hydroformylation reaction is 323 to 573 K, and the reaction pressure is 0.05 to 20.0 MPa.

In a preferred embodiment, the organic ligand polymer with hierarchical porosity has a specific surface area of 200 to 2000 $m^2/g$, a pore volume of 0.5 to 5.0 $cm^3/g$, and a pore size distribution of 0.5 to 100.0 nm.

In a preferred embodiment, when the reactor is a fixed bed or a trickle bed, the olefin hydroformylation reaction is carried out on the solid heterogeneous catalyst continuously, the resultant liquid product continuously flows out of the reactor and is collected by a product-collection tank at a temperature of 255-298 K; when the reactor is an autoclave reactor, the olefin hydroformylation reaction is carried out intermittently, the resultant liquid product is obtained by separation from the solid heterogeneous catalyst through filtration, and the obtained liquid product is further processed by flash evaporation or rectification, so as to obtain aldehyde products having high purity.

In a preferred embodiment, the metal component accounts for 0.01 to 5.0% based on the total weight of the solid heterogeneous catalyst.

In a preferred embodiment, the organic ligand polymer is a polymer formed by polymerization of an organic phosphine ligand monomer containing P and vinyl group and optional N.

The advantageous effects of the invention include, but not limited to the following aspects:

As compared with the current techniques for hydroformylation reaction, in the invention, the reaction process and device are simple, and thus the reaction can be carried out in common fixed beds, trickle beds, or autoclave reactors, since the novel solid heterogeneous catalyst is used; the separation of the catalyst is simple, and the separation of the catalyst from the product is unnecessary in fixed bed and trickle bed, and in autoclave reactor only simple filtration is required; the catalyst is easy to be recovered and can be recycled; the reaction substrates have broad sources, and are suitable for various olefins of $C_2$ to $C_{18}$; the production process of the catalyst is simple, the catalyst has stable hydroformylation properties and a high yield. The invention solves the problems in prior art, such as the loss of the metal component, the loss of the ligand, or the difficulty of recovery and recycle of the catalyst, and thus has a broad prospect in industrial applications.

BRIEF DESCRIPTION OF DRAWINGS

FIG. 1 is a reaction flow chart of an olefin hydroformylation reaction performed continuously according to the invention.

DESCRIPTION OF REFERENCE NUMERALS IN THE FIGURE

1: pressure gauge; 2: purification tank; 3: cut-off valve; 4: pressure regulator valve; 5: cut-off valve; 6: pressure gauge; 7: purification tank; 8: cut-off valve; 9: pressure regulator valve; 10: mass flowmeter; 11: cut-off valve; 12: pump; 13: pressure gauge; 14: cut-off valve; 15: mass flowmeter; 16: pressure gauge; 17: one-way check valve; 18: mixer; 19: preheater; 20: reactor (fixed bed or trickle bed); 21: collection tank; 22: discharge valve; 23: back pressure valve; 24: flowmeter

DETAILED DESCRIPTION OF EMBODIMENTS

The invention realizes a high activity heterogeneous hydroformylation reaction by using a novel solid heterogeneous catalyst, which is consisted of a metal component and an organic ligand polymer with hierarchical porosity (i.e. with hierarchical porosity comprising macropores, mesopores, and micropores). The organic ligand polymer with the hierarchical porosity acts both of a support and a ligand, so as to ensure that the metal active component as a homogeneous catalyst can exist in the pores of the polymer support stably, and thereby the solid heterogeneous catalyst is formed. The problems in the separation of the catalyst from the product and in recycle of the catalyst can be solved by using this solid heterogeneous catalyst system. The method comprises subjecting olefins 1 and $CO/H_2$ mixed gas to the olefin hydroformylation reaction in a reactor, such as a fixed bed, a trickle bed, or an autoclave reactor, in the presence of the solid heterogeneous catalyst.

In one preferred aspect, the invention provides a method for catalyzing hydroformylation reaction using a solid heterogeneous catalyst, the method can include, but not limited to, the following characteristic aspects.

(1) The solid heterogeneous catalyst used is consisted of a metal component and an organic ligand polymer with hierarchical porosity. Preferably, the metal component is one or more of Rh, Ir or Co, the organic ligand polymer with the hierarchical porosity is a polymer formed by polymerization of an organic ligand monomer containing P and alkenyl group and optional N, for example, by solvothermal polymerization. The organic ligand polymer having the hierarchical porosity is preferably a polymer formed by solvothermal polymerization of an organic phosphine ligand monomer containing P and alkenyl group and optional N. Preferably, the metal component accounts for 0.02 to 5.0% of the total weight of the solid heterogeneous catalyst. Preferably, the organic ligand polymer with hierarchical porosity has a specific surface area of 200 to 2000 $m^2/g$, a pore volume of 0.5 to 5.0 $cm^3/g$, and a pore size distribution of 0.5 to 100.0 nm.

(2) The olefin used for the olefin hydroformylation reaction may be one or a mixed olefin of $C_2$ to $C_{18}$ olefins. Preferably, when the olefin is a $C_2$ to $C_3$ gaseous olefin, it is fed in the form of gas directly, and when the olefin is a $C_4$ to $C_{18}$ liquid olefin, it is transported into a reaction system by a high-pressure pump.

(3) The olefin hydroformylation reaction can be carried out in a fixed bed, a trickle bed, or an autoclave reactor. That is to say, the olefin hydroformylation reaction can be carried out intermittently or continuously.

(4) The conditions of the olefin hydroformylation reaction may be preferably as follows: a reaction temperature of 323 to 573K (i.e. 50 to 300° C.), more preferably 353 to 573K; a reaction pressure of 0.05 to 20.0 MPa, more preferably 0.5 to 10.0 MPa. Preferably, the molar ratio of the olefin to the $CO/H_2$ mixed gas is 0.1:1 to 1:1, wherein the volume ratio of CO to $H_2$ in the $CO/H_2$ mixed gas is generally 1:1. Preferably, when the olefin is fed as a gas, the volume space velocity of the gas olefin is 100 to 20000 $h^{-1}$, more preferably 500 to 10000 $h^{-1}$; when the olefin is fed in a liquid form, the mass space velocity of the liquid olefin is 0.01 to 10 $h^{-1}$, more preferably 0.1 to 10 $h^{-1}$; the stirring speed of the slurry bed is 200 to 1000 rpm.

(5) Preferably, when the olefin hydroformylation reaction is carried out in a fixed bed or a trickle bed, the hydroformylation reaction is carried out on the solid catalyst continuously, the resultant liquid product continuously flows out of the reactor and is collected by a product-collection tank at a temperature of 255-298 K; when the olefin hydroformylation reaction is carried out in an autoclave reactor, the olefin hydroformylation reaction is carried out intermittently, the resultant liquid product can be separated from the solid heterogeneous catalyst by simple filtration, for example. More preferably, the obtained liquid products can be further processed by flash evaporation or rectification, or the like, according to the different boiling temperatures thereof, so as to obtain aldehyde products with high purity.

The invention also provides a flow chart of catalyzing the hydroformylation reaction by the novel heterogeneous catalyst, as shown in FIG. 1. Syngas from a steel cylinder passes through a pressure gauge 1 for showing the total pressure, flows through a purification tank 2 for purifying the gas, passes through a cut-off valve 3, passes through a pressure regulator 4 for regulating the pressure, passes through a cut-off valve 5, passes through a pressure gauge 16 for showing the pressure prior to the mass flowmeter, and then passes through a check valve 17 for controlling the flow rate of the syngas. A gaseous olefin (e.g. $C_2$-$C_3$) from a steel cylinder passes through a pressure gauge 6 for showing the total pressure, flows through a purification tank 7 for purifying the gas, passes through a cut-off valve 8, passes through a pressure regulator 9 for regulating the pressure, passes through a mass flowmeter 10 for controlling the flow rate of the gaseous olefin, passes through a cut-off valve 11; a liquid olefin (e.g. $C_4$-$C_{18}$) passes through a high-pressure metering pump to increase to a desired pressure, passes through a pressure gauge 13 for showing the pressure of the liquid olefin, passes through a cut-off valve 14. The syngas and the gaseous olefin or the liquid olefin are mixed sufficiently in a mixer 18, preheated by a preheater 19, and then enter a reactor 20 charged with the solid heterogeneous catalyst, to perform the hydroformylation reaction. The product is collected in a collection tank 21, and subjected to gas-liquid separation. Thereafter, the reaction pressure is controlled by a back pressure valve 23. The tail gas is metered by a flowmeter 24, and then is exhausted. The liquid product passes through a cut-off valve 22 intermittently, and then is discharged, weighted and analyzed.

In one preferred aspect, the method for producing the solid heterogeneous catalyst used in the invention is as follows.

1) At a temperature of 293 to 473 K and in an inert gas (such as nitrogen or argon) protective atmosphere, an appropriate amount of radical initiator is added to an organic solvent of an organic ligand monomer containing P and alkenyl group and optional N, and stirred for 0.5-100 hours. Here, the organic solvent used may be benzene, toluene, tetrahydrofuran, methanol, ethanol, or trichloromethane. The radical initiator used may be cyclohexanone peroxide, dibenzoyl peroxide, tert-butyl hydroperoxide, azodiisobutyronitrile, or azodiisoheptonitrile.

2) At a temperature of 293 to 473 K and in a protective atmosphere of inert gas (such as nitrogen or argon), the stirred solution mentioned above is kept standing for 10-100 hours, to carry out the polymerization reaction.

3) The solvent is drawn off from the reacted mixture at room temperature under vacuum, so as to obtain an organic ligand polymer with hierarchical porosity.

4) The above-mentioned organic ligand polymer with the hierarchical porosity is put into an organic solvent (which may be the same as the above-mentioned organic solvents) containing a metal component, such as one or more of Rh, Ir or Co. It is stirred at a temperature of 293 to 473 K and in a protective atmosphere of inert gas (such as nitrogen or argon) for 0.5-100 hours. After stirring, it is cooled to the room temperature, the solvent is drawn off at room temperature under vacuum, and thereby the desired solid heterogeneous catalyst used in the olefin hydroformylation reaction is obtained.

In the production of the catalyst of the invention, the organic ligand monomer used can include, but not limited to, one or more of the followings:

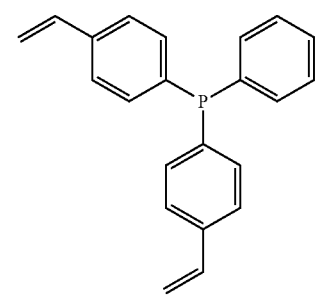
L-1
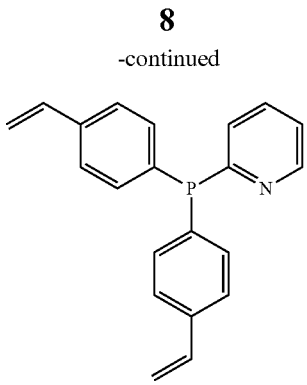
L-6
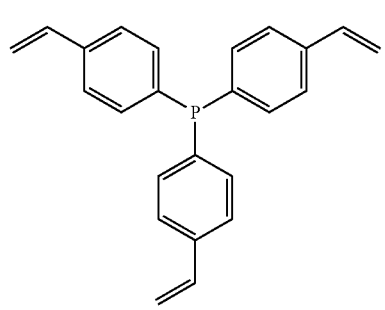
L-2
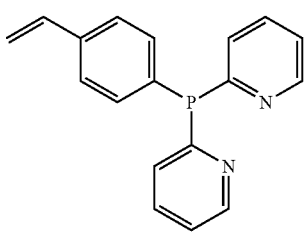
L-7
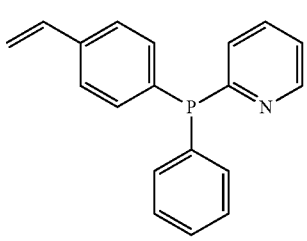
L-8
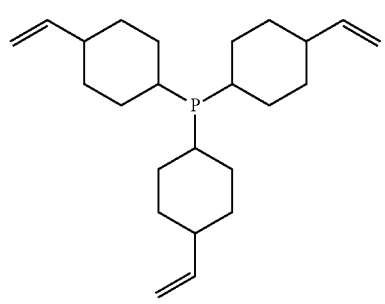
L-3
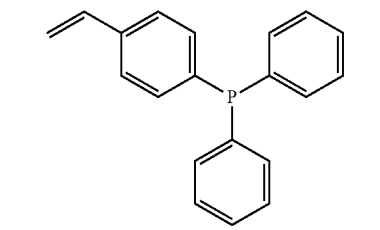
L-4
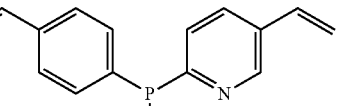
L-9
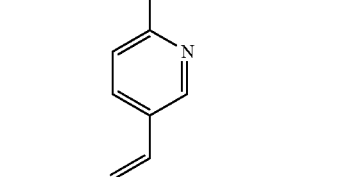
L-10
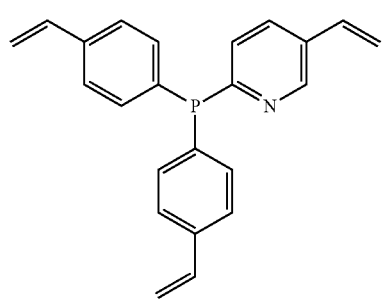
L-5
L-11

-continued

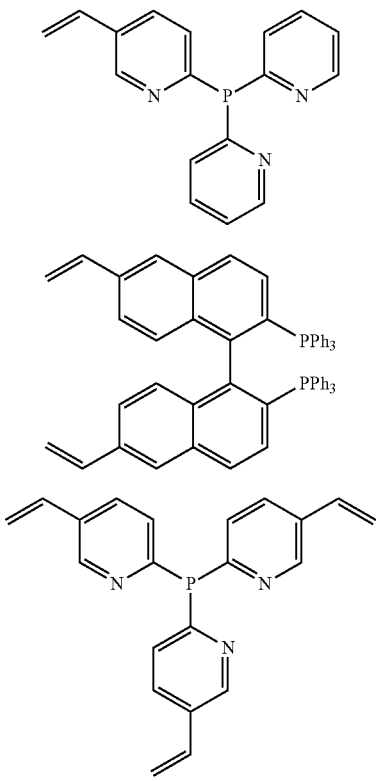

L-12

L-13

L-14

In order to explain the production method of the catalyst and the use thereof in the olefin hydroformylation reaction better, examples for the production of some catalyst samples (in which only tri(4-vinylphenyl)phosphine monomer (i.e. the monomer L-2 mentioned above) is used as the exemplary organic ligand monomer for explanation) and use thereof in reaction process are provided below. However, the invention is not limited to the Examples listed. Unless otherwise indicated, the "percent" used in this application is by weight.

In the following Examples, all raw materials are as follows.

$H_2/CO$ mixed gas (containing 50 vol. % $H_2$ and 50 vol. % CO): Zhonghao Guangming Chemical Industry Research & Design Institute Ltd.

ethylene: Zhonghao Guangming Chemical Industry Research & Design Institute Ltd., purity≥99.999 vol. % propylene: Zhonghao Guangming Chemical Industry Research & Design Institute Ltd., purity≥99.999 vol. %

1-octene: Shanghai Chemical Reagent Co., analytical pure 1-decene: Shanghai Chemical Reagent Co., analytical pure 1-dodecene: Shanghai Chemical Reagent Co., analytical pure tri(4-vinylphenyl)phosphine: synthesized by Zhejiang University, chemical pure The measurements of the specific surface area and the pore size distribution of samples were performed on an Autosorb-1 adsorption analyzer of Quantachrome Instruments Co. Before test, the samples were pretreated at 373 K for 20 hours. A $N_2$ adsorption-desorption test was carried out at a liquid nitrogen temperature of 77 K.

Example 1

10.0 g tri(4-vinylphenyl)phosphine was dissolved in 100.0 ml tetrahydrofuran at 298 K under a protective atmosphere of nitrogen gas. 1.0 g radical initiator azodiisobutyronitrile was added into the above solution, and stirred for 2 hours. The stirred solution was kept standing at 373 K under a protective atmosphere of nitrogen gas for 24 h. Then it was cooled to room temperature, the solvent was drawn off at room temperature (about 298 K) under vacuum, and thereby a P-containing ligand polymer with hierarchical porosity was formed by polymerization from tri(4-vinylphenyl)phosphine via solvothermal method. The technical route for the polymerization of the tri(4-vinylphenyl)phosphine ligand polymer support in this example was shown as follows:

wherein the polymerization degree n was 450-550, a hierarchical porosity comprising macropores, mesopores, and micropores was contained, the BET specific surface area measured was 981 $m^2/g$, the pore volume was 1.45 $cm^3/g$, and the pore size distribution was 0.5 to 100.0 nm.

50.10 mg of dicarbonylacetylacetonato rhodium (I) was dissolved into a three-necked flask charged with 100.0 ml of tetrahydrofuran at 298 K under a protective atmosphere of nitrogen gas by stirring 1.0 g of the P-containing ligand polymer having the hierarchical porosity prepared above was added thereto. This mixture was stirred at 298 K under a protective atmosphere of nitrogen gas for 24 hours, then the solvent was drawn off at room temperature under vacuum, and thereby a metal Rh solid heterogeneous catalyst supported by the P-containing ligand polymer itself having the hierarchical porosity was obtained. The solid heterogeneous catalyst supported by the P-containing ligand polymer itself having the hierarchical porosity prepared above was charged into a fixed bed reactor. Ethylene gas as olefin and CO/$H_2$ mixed gas (in which the volume ratio of $H_2$:CO=1:1) in molar ratio of 1:2 were charged thereto. The reaction was started under following conditions: at 393K, under 1.0 MPa, at a volume space velocity of the olefin gas of 1000 $h^{-1}$, at a volume space velocity of the CO/$H_2$ mixed gas of 2000 $h^{-1}$. The resultant liquid product propylaldehyde was collected in a cold trap collection tank. The liquid product was analyzed by an HP-7890N gas chromatograph equipped with an HP-5 capillary column and an FID detector, using ethanol as the internal standard. The tail gas of the reaction was on-line analyzed by an HP-7890N gas chromatograph equipped with a Porapak-QS column and a TCD detector. The results were shown in Table 1.

Example 2

Concerning the synthesis of the tri(4-vinylphenyl)phosphine ligand polymer support, see Example 1. 0.5 mg of dicarbonylacetylacetonato rhodium (I) was dissolved into a three-necked flask charged with 100.0 ml of tetrahydrofuran at 298 K under a protective atmosphere of nitrogen gas by stirring. 1.0 g of the P-containing ligand polymer having the hierarchical porosity prepared above was added thereto. This mixture was stirred at 298 K under a protective atmosphere of nitrogen gas for 24 hours, then the solvent was drawn off at room temperature under vacuum, and thereby a solid heterogeneous catalyst of metal Rh-supported by the P-containing ligand polymer itself having the hierarchical porosity was obtained. The solid heterogeneous catalyst of metal Rh-supported by the P-containing ligand polymer itself having the hierarchical porosity prepared above was added into a fixed bed reactor. Ethylene gas as olefin raw material and $CO/H_2$ mixed gas (in which the volume ratio of $H_2:CO=1:1$) in molar ratio of 1:2 were charged thereto. The reaction was started under the following conditions: at 393K, under 3.0 MPa, at a volume space velocity of the olefin gas of 2000 $h^{-1}$, at a volume space velocity of the $CO/H_2$ mixed gas of 4000 $h^{-1}$. The resultant liquid product propylaldehyde was collected in a cold trap collection tank. The liquid product was analyzed by an HP-7890N gas chromatograph equipped with an HP-5 capillary column and an FID detector, using ethanol as the internal standard. The tail gas of the reaction was on-line analyzed by an HP-7890N gas chromatograph equipped with a Porapak-QS column and a TCD detector. The results were shown in Table 1.

Example 3

Concerning the synthesis of the tri(4-vinylphenyl)phosphine ligand polymer support, see Example 1. 12.53 mg of dicarbonylacetylacetonato rhodium (I) was dissolved into a three-necked flask charged with 100.0 ml of tetrahydrofuran at 298 K under a protective atmosphere of nitrogen gas by stirring. 1.0 g of the P-containing ligand polymer having the hierarchical porosity prepared above was added thereto. This mixture was stirred at 298 K under a protective atmosphere of nitrogen gas for 24 hours, then the solvent was drawn off at room temperature under vacuum, and thereby a solid heterogeneous catalyst of metal Rh supported by the P-containing ligand polymer itself having the hierarchical porosity was obtained. The solid heterogeneous catalyst prepared above was added into a fixed bed reactor. Propylene gas as olefin raw material and $CO/H_2$ mixed gas (in which the volume ratio of $H_2:CO=1:1$) in molar ratio of 1:2 were charged thereto. The reaction was started under the following conditions: at 393K, under 1.0 MPa, at a volume space velocity of the olefin gas of 1000 $h^{-1}$, at a volume space velocity of the $CO/H_2$ mixed gas of 2000 $h^{-1}$. The resultant liquid product butylaldehyde was collected in a cold trap collection tank. The liquid product was analyzed by an HP-7890N gas chromatograph equipped with an HP-5 capillary column and an FID detector, using ethanol as the internal standard. The tail gas of the reaction was on-line analyzed by an HP-7890N gas chromatograph equipped with a Porapak-QS column and a TCD detector. The results were shown in Table 1.

Example 4

Concerning the synthesis of the tri(4-vinylphenyl)phosphine ligand polymer supporter, see Example 1. 12.53 mg of dicarbonylacetylacetonato rhodium (I) was dissolved into a three-necked flask charged with 100.0 ml of tetrahydrofuran at 298 K under a protective atmosphere of nitrogen gas by stirring. 1.0 g of the P-containing ligand polymer having the hierarchical porosity prepared above was added thereto. This mixture was stirred at 298 K under a protective atmosphere of nitrogen gas for 24 hours, then the solvent was drawn off at room temperature under vacuum, and thereby a solid heterogeneous catalyst of metal Rh supported by the P-containing ligand polymer itself having the hierarchical porosity was obtained. 1.2 g of 1-octene and 4.8 g of toluene as a solvent were weighed out and placed in an autoclave reactor, then the solid heterogeneous catalyst of Rh supported by the P-containing ligand polymer itself having the hierarchical porosity prepared above was added into the autoclave reactor. Once the reactor was closed and an airtight test was performed, syngas (in which the volume ratio of $H_2:CO=1:1$) was charged, the air in the reactor was replaced 3 times, and then the syngas was continuously fed at 393 K under 1.0 MPa, until the reaction pressure was remained unchanged. When the stirring speed of the autoclave was 1000 rpm, the reaction was started. After 4 hours, the autoclave was opened, and the liquid product was extracted from the autoclave reactor, while the catalyst may be remained in the autoclave for recycle. The liquid product was analyzed by an HP-7890N gas chromatograph equipped with an HP-5 capillary column and an FID detector, using ethanol as the internal standard. The tail gas of the reaction was on-line analyzed by an HP-7890N gas chromatograph equipped with a Porapak-QS column and a TCD detector. The results were shown in Table 1.

Example 5

Concerning the synthesis of the tri(4-vinylphenyl)phosphine ligand polymer supporter, see Example 1. 12.53 mg of dicarbonylacetylacetonato rhodium (I) was dissolved into a three-necked flask charged with 100.0 ml of tetrahydrofuran at 298 K under a protective atmosphere of nitrogen gas by stirring. 1.0 g of the P-containing ligand polymer having the hierarchical porosity prepared above was added therein. This mixture was stirred at 298 K under a protective atmosphere of nitrogen gas for 24 hours, then the solvent was drawn off at room temperature under vacuum, and thereby a solid heterogeneous catalyst of metal Rh supported by the P-containing ligand polymer itself having the hierarchical porosity was obtained. 1.2 g of 1-decene and 4.8 g of toluene as a solvent were weighed out and placed in an autoclave reactor, then the solid heterogeneous catalyst of metal Rh-supported by the P-containing ligand polymer itself having the hierarchical porosity prepared above was added into the autoclave reactor. Once the reactor was closed and an airtight test was performed, syngas (in which the volume ratio of $H_2:CO=1:1$) was charged, the air in the reactor was replaced 3 times, and then the syngas was continuously fed at 393 K under 1.0 MPa, until the reaction pressure was remained unchanged. When the stirring speed of the autoclave was 1000 rpm, the reaction was started.

After 4 hours, the autoclave was opened, and the liquid product was separated from the catalyst via filtration from the autoclave reactor, while the catalyst may be remained in the autoclave for recycle. The liquid product was analyzed by an HP-7890N gas chromatograph equipped with an HP-5 capillary column and an FID detector, using ethanol as the internal standard. The tail gas of the reaction was on-line analyzed by an HP-7890N gas chromatograph equipped with a Porapak-QS column and a TCD detector. The results were shown in Table 1.

Example 6

Concerning the synthesis of the tri(4-vinylphenyl)phosphine ligand polymer supporter, see Example 1. 12.53 mg of dicarbonylacetylacetonato rhodium (I) was dissolved into a three-necked flask charged with 100.0 ml of tetrahydrofuran at 298 K under a protective atmosphere of nitrogen gas by stirring. 1.0 g of the P-containing ligand polymer having the hierarchical porosity prepared above was added thereto. This mixture was stirred at 298 K under a protective atmosphere of nitrogen gas for 24 hours, then the solvent was drawn off at room temperature under vacuum, and thereby a solid heterogeneous catalyst of metal Rh supported by the P-containing ligand polymer itself having the hierarchical porosity was obtained. The solid heterogeneous catalyst of Rh supported by the P-containing ligand polymer itself having the hierarchical porosity prepared above was added into a trickle bed reactor. Syngas (in which the volume ratio of $H_2:CO=1:1$) was charged. The reaction was started under the following conditions: at 393K, under 3.0 MPa, at a space velocity of the syngas of 2000 at a mass space velocity of a liquid olefin (LHSV)=0.5 $h^{-1}$, wherein 1-dodecene liquid material was pumped into the reactor through a high-pressure metering pump. The liquid product aldehyde was collected in a cold trap collection tank. The liquid product was analyzed by an HP-7890N gas chromatograph equipped with an HP-5 capillary column and an FID detector, using ethanol as the internal standard. The tail gas of the reaction was on-line analyzed by an HP-7890N gas chromatograph equipped with a Porapak-QS column and a TCD detector. The results were shown in Table 1.

Example 7

Concerning the synthesis of the tri(4-vinylphenyl)phosphine ligand polymer supporter, see Example 1. 12.53 mg of dicarbonylacetylacetonato rhodium (I) was dissolved into a three-necked flask charged with 100.0 ml of tetrahydrofuran at 298 K under a protective atmosphere of nitrogen gas by stirring. 1.0 g of the P-containing ligand polymer having the hierarchical porosity prepared above was added thereto. This mixture was stirred at 298 K under a protective atmosphere of nitrogen gas for 24 hours, then the solvent was drawn off at room temperature under vacuum, and thereby a solid heterogeneous catalyst of metal Rh supported by the P-containing ligand polymer itself having the hierarchical porosity was obtained. The solid heterogeneous catalyst of Rh supported by the P-containing ligand polymer itself having the hierarchical porosity prepared above was added into a trickle bed reactor. Syngas (in which the volume ratio of $H_2:CO=1:1$) was charged. The reaction was started under the following conditions: at 393K, under 3.0 MPa, at a space velocity of the syngas of 2000 $h^{-1}$, at a LHSV=0.5 $h^{-1}$, wherein 1-octadecene liquid material was pumped into the reactor through a high-pressure metering pump. The liquid product aldehyde was collected in a cold trap collection tank. The liquid product was analyzed by an HP-7890N gas chromatograph equipped with an HP-5 capillary column and an FID detector, using ethanol as the internal standard. The tail gas of the reaction was on-line analyzed by an HP-7890N gas chromatograph equipped with a Porapak-QS column and a TCD detector. The results were shown in Table 1.

TABLE 1 the olefin hydroformylation reaction properties on the novel heterogeneous catalyst

| Example | Olefin conversion, (%) | Selectivity, (wt %) | | | ratio of normal product to isomeric product (n/i) |
| --- | --- | --- | --- | --- | --- |
| | | alkanes | isomeric olefins | product aldehyde | |
| Example 1 | 99.8 | 0.35 | — | 99.65 | — |
| Example 2 | 99.9 | 0.23 | — | 99.77 | — |
| Example 3 | 97.33 | 1.58 | — | 98.42 | 3.06 |
| Example 4 | 97.78 | 2.47 | 16.03 | 81.49 | 3.11 |
| Example 5 | 99.22 | 0.72 | 15.76 | 83.53 | 3.38 |
| Example 6 | 89.27 | 1.77 | 21.42 | 76.81 | 6.29 |
| Example 7 | 87.39 | 0.78 | 25.42 | 73.8 | 7.59 |

As can be known from the results in Table 1 above, in the method for olefin hydroformylation reaction using novel solid heterogeneous catalyst provided by the invention, the reaction process and device are simple, and thus the reaction can be carried out in normal fixed beds, trickle beds, or autoclave reactors; it is suitable for various olefins of $C_2$ to $C_{18}$; the hydroformylation reaction has stable properties with a high yield. The invention solves the problems of the prior art, such as loss of the metal component, loss of the ligand, or the difficulty for recovery and recycle of the catalyst, and thus has a wide prospect in industrial applications.

The invention has been described in details above, but the invention is not limited to the particular embodiments described herein. Those skilled in the art will understand that other modifications and variations may be made, without departing the scope of the invention. The scope of the invention is defined by the appended claims.

The invention claimed is:

1. A method for olefin hydroformylation reaction comprising subjecting olefins and $CO/H_2$ mixed gas to the olefin hydroformylation reaction in a reactor in the presence of a solid heterogeneous catalyst, which consisted of a metal component and an organic ligand polymer with hierarchical porosity, wherein the metal component is one or more of Rh, Ir or Co, the organic ligand polymer is a polymer formed by polymerization of an organic ligand monomer containing P and alkenyl group and optional N, the metal component forms coordinated bonds with the P or N atom in backbone of the organic ligand polymer and exists in a monoatomic dispersion state in the solid heterogeneous catalyst.

2. The method according to claim 1, wherein the olefin is one or more of $C_2$ to $C_{18}$ olefins, and the molar ratio of the olefin to the $CO/H_2$ mixed gas is 0.1:1 to 1:1.

3. The method according to claim 1, wherein when the olefin is a $C_2$ to $C_3$ gaseous olefin, it is fed in the form of gas directly at a volume space velocity of 100 to 20000 $h^{-1}$; and when the olefin is a $C_4$ to $C_{18}$ liquid olefin, it is transported into a reaction system by a high-pressure pump at a mass space velocity of 0.01 to 10 $h^{-1}$.

4. The method according to claim 1, wherein the reactor is a fixed bed, a trickle bed, or an autoclave reactor.

5. The method according to claim 1, wherein the olefin hydroformylation reaction is carried out intermittently or continuously.

6. The method according to claim 1, wherein the reaction temperature of the olefin hydroformylation reaction is 323 to 573 K, and the reaction pressure is 0.05 to 20.0 MPa.

7. The method according to claim 1, wherein the organic ligand polymer with hierarchical porosity has a specific surface area of 200 to 2000 m$^2$/g, a pore volume of 0.5 to 5.0 cm$^3$/g, and a pore size distribution of 0.5 to 100.0 nm.

8. The method according to claim 4, wherein when the reactor is a fixed bed or a trickle bed, the olefin hydroformylation reaction is carried out on the solid heterogeneous catalyst continuously, the resultant liquid product continuously flows out of the reactor and is collected by a product-collection tank at a temperature of 255-298 K; and when the reactor is an autoclave reactor, the olefin hydroformylation reaction is carried out intermittently, the resultant liquid product is obtained by separation from the solid heterogeneous catalyst through filtration, and the liquid product thus obtained is further processed by flash evaporation or rectification, so as to obtain aldehyde products with high purity.

9. The method according to claim 1, wherein the metal component accounts for 0.01 to 5.0% of the total weight of the solid heterogeneous catalyst.

10. The method according to claim 1, wherein the organic ligand polymer is a polymer formed by polymerization of an organic phosphine ligand monomer containing P and an alkenyl group and optional N.

\* \* \* \* \*